US005731203A

United States Patent [19]
Handley, III

[11] Patent Number: 5,731,203
[45] Date of Patent: *Mar. 24, 1998

[54] METHOD FOR REGENERATION OF CONIFEROUS PLANTS BY SOMATIC EMBRYOGENESIS

[75] Inventor: Levis W. Handley, III, Charleston, S.C.

[73] Assignee: Westvaco Corporation, New York, N.Y.

[*] Notice: The term of this patent shall not extend beyond the expiration date of Pat. Nos. 5,413,930, 5,491,090 and 5,506,136.

[21] Appl. No.: 664,936

[22] Filed: Jun. 14, 1996

[51] Int. Cl.$^6$ .................. A01H 4/00; A01H 7/00
[52] U.S. Cl. .......... 435/430.1; 435/422; 435/430; 435/431
[58] Field of Search .................. 435/422, 430, 435/430.1, 431

[56] References Cited

U.S. PATENT DOCUMENTS

| | | | |
|---|---|---|---|
| 4,957,866 | 9/1990 | Gupta et al. | 435/422 |
| 5,034,326 | 7/1991 | Pullman et al. | 435/422 |
| 5,036,007 | 7/1991 | Gupta et al. | 435/422 |
| 5,183,757 | 2/1993 | Roberts | 435/422 |
| 5,187,092 | 2/1993 | Uddin | 435/422 |
| 5,236,841 | 8/1993 | Gupta et al. | 435/422 |
| 5,294,549 | 3/1994 | Pullman et al. | 435/422 |
| 5,413,930 | 5/1995 | Becwar et al. | 435/422 |
| 5,491,090 | 2/1996 | Handley et al. | 435/422 |
| 5,506,136 | 4/1996 | Becwar et al. | 435/422 |
| 5,534,433 | 7/1996 | Coke | 435/431 |

OTHER PUBLICATIONS

Becwar, M.R., R. Nagmani, and S.R. Wann. Initiation of embryogenic cultures and somatic embryo development in loblolly pine (*Pinus taeda*). *Canadian Journal of Forest Research* 20:810–817, 1990.

Gupta, P.K. and D.J. Durzan. Shoot multiplication from mature trees of Douglas-fir (*Pseudotsuga menziesii*) and sugar pine (*Pinus lambertiana*). *Plant Cell Reports* 4:177–179, 1985.

Hakman, I. and S. von Arnold. Plantlet regeneration through somatic embryogenesis in *Picea abies* (Norway spruce). *Journal of Plant Physiology* 121:149–158, 1985.

Hakman, I., L. C. Fowke, S. von Arnold, and T. Eriksson. The development of somatic embryos in tissue cultures initiated from immature embryos of *Picea abies* (Norway spruce). *Plant Science* 38:53–59, 1985.

Handley, L.W., M.R. Becwar, E.E. Chesick, J.E. Coke, A.P. Godbey and M.R. Rutter. Research and Development of commercial tissue culture systems in loblolly pine. *TAPPI Journal* vol. 78, No. 5; pp. 169–175, 1994.

Jain, S.M., N. Dong, and R.J. Newton. Somatic embryogenesis in slash pine (*Pinus elliottii*) from immature embryos cultured in vitro. *Plant Science* 65:233–241, 1989.

Preston, R.J. North American Trees, 4th edition. Iowa State Univ. Press, Ames. pp. 4–7, 1989.

Schenk, R.U. and A.C. Hildebrandt. Medium and techniques for induction and growth of monocotyledonous and dicotyledonous plant cell cultures. *Canadian Journal of Botany* 50:199–204, 1972.

Tautorus, T.E., L.C. Fowke, and D.I. Dunstant. Somatic embryogenesis in conifers. *Canadian Journal of Botany* 69–1873–1899, 1991.

von Arnold, S. and I. Hakman. Regulation of somatic embryo development in *Picea abies* by abscisic acid (ABA). *Journal of Plant Physiology* 132–164–169, 1988.

*Primary Examiner*—Irene Mark
*Assistant Examiner*—Janet M. Kerr
*Attorney, Agent, or Firm*—Daniel B. Reece, IV; Terry B. McDaniel; Richard L. Schmalz

[57] ABSTRACT

This invention relates to a method for regeneration of coniferous plants. In particular, this invention relates to an improved method for developing viable stage 3 embryos from embryogenic cultures for somatic embryogenesis processes for plants of the genus Pinus and Pinus interspecies hybrids. This method is well suited for producing clonal planting stock useful for reforestation.

12 Claims, No Drawings

METHOD FOR REGENERATION OF CONIFEROUS PLANTS BY SOMATIC EMBRYOGENESIS

FIELD OF THE INVENTION

This invention relates to a method for regeneration of coniferous plants. In particular, this invention relates to an improved method for developing viable stage 3 embryos from embryogenic cultures for somatic embryogenesis processes for plants of the genus Pinus and Pinus interspecies hybrids. This method is well suited for producing clonal planting stock useful for reforestation.

BACKGROUND OF THE INVENTION

Propagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. These qualities endow somatic embryogenesis processes with the potential to produce large numbers of individual clones for reforestation purposes.

It was not until 1985 that somatic embryogenesis was discovered in conifers (Hakman et al. 1985) and the first viable plantlets were regenerated from conifer somatic embryos (Hakman and von Arnold 1985). Since 1985, conifer tissue culture workers throughout the world have pursued the development of somatic embryogenesis systems capable of regenerating plants. The goal of much of this work is to develop conifer somatic embryogenesis as an efficient propagation system for producing clonal planting stock en masse. Additionally, the embryogenic system interfaces very well with genetic engineering techniques for production of transgenic clonal planting stock of conifers.

The two most economically important conifer genera are Picea (spruce) and Pinus (pine). Those working in conifer somatic embryogenesis have found that there is a striking difference between Picea conifers and Pinus conifers as to the ease with which somatic embryogenesis can be induced and plants regenerated (Tautorus et al. 1991). In fact, when one measures the respective levels of achievement in the art of conifer somatic embryogenesis among species of these two important genera, it is clear that significantly more success has been obtained with Picea than with Pinus. Indeed, the recalcitrance of embryogenic cultures of Pinus species is well documented. This is especially true for pines commonly found in the southeastern United States (known in the industry as Southern yellow pines).

Nevertheless, researchers working with Pinus species plants have recently achieved some important advances. In commonly assigned U.S. Pat. Nos. 5,413,930 and 5,506,136 (which are hereby incorporated by reference), Becwar et al. disclose multi-step methods that are able to complete the entire somatic embryogenesis regenerative process, from explant collection to planting, for historically recalcitrant Southern yellow pines (i.e., *Pinus taeda, Pinus serotina, Pinus palustris*, and *Pinus elliottii*), *Pinus rigida*, and hybrids thereof.

In commonly assigned U.S. Pat. No. 5,491,090 (which is hereby incorporated by reference), Handley et al. improved upon the above-noted processes by teaching a method which enables its practitioners to replace the semi-solid maintenance culture media taught by Becwar et al. with established liquid suspension culture media.

While the methods taught in U.S. Pat. Nos. 5,413,930, 5,491,090, and 5,506,136 have produced thousands of somatic embryos and hundreds of plants in the field, these embryos and plants have often been in relatively low numbers from a range of families or genotypes within a family. Therefore, even though these patented methods have achieved considerable success in both establishing embryogenic cultures of Pinus and in producing large numbers of field grown plants, these methods have proven to be somewhat limited by low embryo development frequencies experienced by different genetic families. Indeed, one of the limiting factors in achieving clonal forestry in these pines has been the inability to produce sufficient numbers of developed embryos from some of the very best genetic material and, subsequently, production of somatic embryo plants for field testing and eventual clonal deployment (Handley et al. 1994). Simply put, a major problem limiting commercial development of the above-noted methods is that they tend to exhibit relatively low embryo development frequencies in certain explants due to the genetic specificity of those explants.

The present invention corrects this problem by teaching an improved method which increases the frequency of embryo development from 60% to 200% when compared to the methods taught in U.S. Pat. Nos. 5,413,930, 5,491,090, and 5,506,136 (see Examples). This improvement is highly significant because it ensures that more embryos are produced to develop more plants, thereby allowing more genotypes to be subsequently available for field testing and production of clonal planting stock.

Having a low frequency of embryo development can severely limit the potential applications of somatic embryogenesis in Pinus species for large-scale production of genetically improved conifers for the following reason. Skilled artisans in the conifer tissue culture field recognize that the use of embryogenic cultures derived from juvenile explants (e.g., zygotic embryos derived from seed) necessitate that the resulting regenerated plants be field tested prior to large scale production. Only selected genotypes which show the potential for producing significant genetic gain in such field tests will subsequently be propagated by somatic embryogenesis. It will, therefore, be necessary to screen numerous genotypes from desirable parents, initiate embryogenic cultures, cryopreserve each genetically different culture, regenerate and develop embryos and plants from each genetically different culture, field test plants from each genotype, and select genotypes for large scale production via somatic embryogenesis.

Low culture development frequencies pose a severe limitation for implementing this strategy in that when few embryos are produced per gram of embryogenic callus (or suspension culture cells) it is almost impossible to obtain sufficient embryos for the necessary field plantings. For example, embryo production at the level of around 5 to 10 embryos per clump of tissue is not commercially adequate. Indeed, lines having embryo development rates this low are usually eliminated from testing (as it is extremely difficult to get these to produce enough embryos for a field test and later production). This invention solves this major problem by increasing the embryo production across a range of lines.

As noted above, another problem plaguing current somatic embryogenesis methods is that it has traditionally been extremely difficult to establish sufficient numbers of embryos from some of the best genetic families of loblolly pine. A series of experiments have shown that, when propagated via the above-noted patented methods, a large percentage of those embryogenic lines exhibited relatively low production numbers. The present method corrects this problem by allowing one to produce large numbers of embryos from a wider range of genetic materials (including materials of very high genetic value).

Somatic embryogenesis processes utilized with conifers (particularly the Pinus species) usually involve seven general steps: 1) culture initiation, 2) culture maintenance, 3) embryo development, 4) embryo maturation, 5) embryo germination, 6) conversion, and 7) plant growth (field planting). The culture media utilized in the respective steps are key components of effective somatic embryogenesis regeneration systems.

U.S. Pat. Nos. 5,413,930, 5,491,090, and 5,506,136 teach the use of semi-solid culture media during the embryo development step. These culture media are generally composed of seven groups of ingredients: inorganic nutrients, vitamins, organic supplements, a carbohydrate source, phytohormones, abscisic acid, and a gelling agent.

The improvement of the present method over the above-noted patented methods is the consequence of three changes in the embryo development step. First, activated carbon is added to the development media. Second, a high level of abscisic acid (110 mg/L to 300 mg/L) is added to the development media. Third, the high concentration of abscisic acid in the development media is maintained throughout the entire development step.

It is known that low levels of abscisic acid (ABA) stimulate embryo development in somatic embryogenic systems (von Arnold and Hakman, 1988). For example, U.S. Pat. No. 4,957,866 teaches a somatic embryogenesis process for coniferous plants wherein the embryo development media contains low concentrations of ABA (about 4.0 to 8.0 mg/L). Likewise, U.S. Pat. No. 5,183,757 claims the use of low levels of ABA (30–40 µM/L or about 8–11 mg/L) in growth (development) media for spruce embryos.

While U.S. Pat. No. 5,187,092 claims the use of "at least 10 µM/L" of ABA in its growth (development) media, it is clear from the specification that the patent actually teaches the use of extremely low ABA concentrations. Indeed, the patent specifies the preferred ABA range as being between 10–30 µM/L (about 3–8 mg/L), with the most preferred level of ABA being about 20 µM/L (about 5.3 mg/L).

U.S. Pat. No. 5,294,549 teaches the employment of a active gibberellin in the development medium. About 1–50 mg/L of ABA is also added to the medium to augment the effect of the gibberellin.

U.S. Pat. No. 5,036,007 teaches the use of low concentrations of ABA (about 20–60 µM/L or about 5–16 mg/L) to formulate media employed in an intermediate embryo development step (which was found to be particularly useful in reproducing Douglas Fir). An essential component of this patented method is the addition of an absorbent material (such as activated carbon) to the development media for the express purpose of gradually reducing the level of available ABA over time.

U.S. Pat. No. 5,034,326 claims the use of development media containing an adsorbent material and about 5–100 mg/L of ABA. Again, it is essential to this method that a sufficient amount of the adsorbent material be included in the development media to guarantee gradual reduction of the ABA concentration over time.

U.S. Pat. No. 5,236,841 also claims the use of development media containing about 5–100 mg/L of ABA. However, instead of employing an adsorbent material to reduce the concentration of ABA over time, this patent teaches an alternative method for reducing the ABA concentration (i.e., repetitive subculturing to fresh development media containing reduced ABA concentrations).

It is vital to note that the present method fundamentally differs from these patented methods in at least two important ways: (1) by teaching the use of significantly higher levels of ABA in the growth media, and (2) by teaching the continued maintenance of these high ABA concentrations throughout the entire development step (thereby not decreasing the concentration of ABA over time).

It is, therefore, an object of the present invention to provide an improved method for developing embryos for use in somatic embryogenesis processes for plants of the genus Pinus and Pinus interspecies hybrids.

Another object of the present invention is to provide an improved method for the regeneration of coniferous plants by somatic embryogenesis.

A further object of the present invention is to provide an improved method for the development of stage 3 somatic embryos from embryogenic tissue cultures from plants of the genus Pinus and Pinus interspecies hybrids so that these embryos can be further induced to germinate and converted to yield viable plants for field planting.

SUMMARY OF THE INVENTION

The above objectives are achieved by the use of an improved method for developing embryos for use in somatic embryogenesis processes employing embryogenic tissues from plants of the genus Pinus and Pinus interspecies hybrids. This method allows the practitioner to develop viable Pinus embryos from a wide range of genetic backgrounds. The improvements in these methods were accomplished via the addition of activated carbon and very high levels of abscisic acid to the development media onto which the embryogenic tissues (or embryogenic cell cultures) are placed and stage 3 embryos developed. The high ABA concentrations are maintained throughout the entire embryo development step.

The method results in improved stage 3 embryo development frequencies, thereby allowing many more vigorous embryos to be obtained. (These embryos can, in turn, be successfully carried through the subsequent stages of the somatic embryogenesis process). Furthermore, the method makes it feasible to include more genotypes from families of high genetic value. As somatic plants produced from these families can be planted in clonal field tests, the likelihood of being able to select highly productive genotypes is greatly increased. In addition, more genotypes can be quickly proliferated via this method for rapid production of clonal planting stock from many selected parents. The employment of previous methods often resulted in a significant number of embryogenic lines exhibiting very low (or zero) embryo development frequencies. While one may still expect that a few lines will fail to produce sufficient numbers of embryos even when using the present improved method, the overall embryo development response across lines is substantially increased.

DESCRIPTION OF THE PREFERRED EMBODIMENT

As noted above, the somatic embryogenesis process utilized with conifers (particularly the Pinus species) can be divided into seven general steps: 1) culture initiation, 2)

culture maintenance, 3) embryo development, 4) embryo maturation, 5) embryo germination, 6) conversion, and 7) plant growth (field planting). The present invention improves upon the methods taught in U.S. Pat. Nos. 5,413,930, 5,491,090, and 5,506,136 by changing and improving the third step (the embryo development step) in those methods. The improved embryo development step comprises:

transferring at least 100 mg of the mass of embryogenic tissue (or, alternatively, at least 30 mg of the liquid embryogenic cell culture) to embryo development medium containing a sufficient amount of nutrients, a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL, and combinations thereof, 20.0 to 70.0 g/l of a sugar selected from the group consisting of glucose, maltose, sucrose, melezitose, and combinations thereof, and wherein the improvement comprises the addition of about 0.1 to about 10.0 g/L of activated carbon, the addition of about 110 to about 300 mg/L of abscisic acid, and the continued maintenance of the abscisic acid concentration; for a sufficient time under suitable environmental conditions to develop stage 3 somatic embryos.

The present method significantly improves the embryo development step by incorporating activated carbon and high levels of phytohormone abscisic acid into the embryo development media, and by maintaining the high ABA concentration in the media over the entire period of the step. These changes significantly increase, across a range of genotypes, the amount of viable embryos developed.

This improved development step for producing stage 3 somatic embryos is employed with the remaining method steps (culture initiation, culture maintenance, embryo maturation, embryo germination, conversion, and plant growth) taught in U.S. Pat. Nos. 5,413,930 and 5,506,136 to create improved methods for producing coniferous plants via somatic embryogenesis. To practice the improved method one follows these steps:

1. placing a suitable explant selected from the group consisting of immature zygotic embryos and megagametophytes containing immature zygotic embryos on culture initiation medium containing a sufficient amount of nutrients, 0.1 to 5.0 mg/L of auxin, 0.1 to 1.0 mg/L of cytokinin, 10.0 to 40.0 g/l of a sugar selected from the group consisting of glucose, maltose, sucrose, melezitose, and combinations thereof, and a level of gelling agent selected from the group consisting of 2.5 to 4.5 g/l of agar, 0.5 to 1.5 g/l of gellan gum, 3.0 to 5.0 g/l of agarose, 1.5 to 3.0 g/l of AGARGEL, and combinations thereof, for 2 to 14 weeks under suitable environmental conditions to grow a culture containing embryogenic tissue;

2. transferring the embryogenic tissue culture to culture maintenance medium containing a sufficient amount of nutrients, 0.1 to 5.0 mg/L of auxin, 0.1 to 1.0 mg/L of cytokinin, 10.0 to 40.0 g/l of a sugar selected from the group consisting of glucose, maltose, sucrose, melezitose and combinations thereof, and a level of gelling agent selected from the group consisting of 6.0 to 9.0 g/l of agar, 1.75 to 3.5 g/l of gellan gum, 6.0 to 8.0 g/l of agarose, 3.5 to 5.0 g/l of AGARGEL, and combinations thereof, for a sufficient amount of time under suitable environmental conditions to develop a mass of embryogenic tissue having a weight of at least 100.0 mg;

3. transferring at least about 100 mg of the mass of embryogenic tissue to embryo development medium containing a sufficient amount of nutrients, a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL, and combinations thereof, 20.0 to 70.0 g/l of a sugar selected from the group consisting of glucose, maltose, sucrose, melezitose, and combinations thereof, and wherein the improvement comprises the addition of about 0.1 to about 10.0 g/L of activated carbon, the addition of about 110 to about 300 mg/L of abscisic acid, and the continued maintainence of the abscisic acid concentration; for a sufficient time under suitable environmental conditions to develop stage 3 somatic embryos;

4. separating the stage 3 somatic embryos from the development medium and partially drying the embryos by exposing the embryos to an atmosphere having a high relative humidity for sufficient time to permit the embryos to lose about 25% to 75% of their pre-dried weight;

5. transferring the partially dried somatic embryos to germination medium containing a sufficient amount of nutrients, up to 10.0 g/l of activated carbon, a level of gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, and 20.0 to 40.0 g/l of a sugar selected from the group consisting of glucose, maltose, sucrose, and combinations thereof, for a sufficient time under suitable environmental conditions to germinate the partially dried embryos;

6. converting the germinated embryos into acclimatized plants; and 7. field planting the acclimatized plants.

Alternatively, one may utilize the improved development step for producing stage 3 somatic embryos with the remaining method steps (culture initiation, culture maintenance, embryo maturation, embryo germination, conversion, and plant growth) taught in U.S. Pat. No. 5,491,090 to create an improved method for producing coniferous plants via somatic embryogenesis. To practice the improved method one follows these steps:

1. placing a suitable explant selected from the group consisting of immature zygotic embryos and megagametophytes containing immature zygotic embryos on culture initiation medium containing a sufficient amount of nutrients, 0.1 to 5.0 mg/L of auxin, 0.1 to 1.0 mg/L of cytokinin, 5.0 to 100.0 g/l of a sugar selected from the group consisting of glucose, maltose, sucrose, melezitose, and combinations thereof, and a level of gelling agent selected from the group consisting of 2.5 to 4.5 g/l of agar, 0.5 to 1.5 g/l of gellan gum, 3.0 to 5.0 g/l of agarose, 1.5 to 3.0 g/l of AGARGEL, and combinations thereof, for 2 to 14 weeks under suitable environmental conditions to grow a culture containing embryogenic tissue;

2. transferring the embryogenic tissue culture to liquid suspension culture maintenance medium containing a sufficient amount of nutrients, 0.1 to 100.0 mg/L of auxin, 0.05 to 10.0 mg/L of cytokinin, 5.0 to 100.0 g/l of a sugar selected from the group consisting of glucose, maltose, sucrose, melezitose and combinations thereof, and about 0.1 to 10.0 g/l of activated carbon, for a sufficient amount of time under suitable environmental conditions to develop a liquid embryogenic cell culture;

3. transferring at least 30 mg of the liquid embryogenic cell culture to embryo development medium containing a sufficient amount of nutrients, a level of gelling agent selected from the group consisting of 6.0 to 12.0 g/l of agar, 1.75 to 4.00 g/l of gellan gum, 6.0 to 8.0 g/l of agarose, 3.5 to 6.0 g/l of AGARGEL, and combinations thereof, 20.0 to 70.0 g/l of a sugar selected from the group consisting of glucose, maltose, sucrose, melezitose, and combinations thereof, and wherein the improvement comprises the addition of about 0.1 to about 10.0 g/L of activated carbon, the addition of about 110 to about 300 mg/L of abscisic acid, and the continued maintainence of the abscisic acid concentration; for a sufficient time under suitable environmental conditions to develop stage 3 somatic embryos;

4. separating the stage 3 somatic embryos from the development medium and partially drying the embryos by exposing the embryos to an atmosphere having a high relative humidity for sufficient time to permit the embryos to lose about 25% to 75% of their pre-dried weight;

5. transferring the partially dried somatic embryos to germination medium containing a sufficient amount of nutrients, up to 10.0 g/l of activated carbon, a level of gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, and 20.0 to 40.0 g/l of a sugar selected from the group consisting of glucose, maltose, sucrose, and combinations thereof, for a sufficient time under suitable environmental conditions to germinate the partially dried embryos;

6. converting the germinated embryos into acclimatized plants; and 7. field planting the acclimatized plants.

This method is generally applicable to somatic tissue obtained from the Pinus species including, but not limited to, the following: *Pinus taeda* (loblolly pine), *P. elliottii* (slash pine), *P. palustris* (longleaf pine), *P. serotina* (pond pine), *P. echinata* (shortleaf pine), *P. clausa* (sand pine), *P. glabra* (spruce pine), *P. rigida* (pitch pine), *P. echinata* (shortleaf pine), *P. nigra* (Austrian pine), *P. resinosa* (red pine), *P. sylvestris* (Scotch pine), *P. banksiana* (jack pine), *P. virginiana* (Virginia pine), *P. radiata* (Monterey pine), *P. contorta* (shore pine), *P. contorta latifolia* (lodgepole pine), *P. ponderosa* (ponderosa pine), *P. leiophylla* (Chihuahua pine), *P. jeffreyi* (Jeffrey pine), and *P. engelmannii* (Apache pine), *P. strobus* (eastern white pine), *P. monticola* (western white pine), and *P. lambertiana* (sugar pine), *P. albicaulis* (whitebark pine), *P. flexilis* (limber pine), *P. strobiformis* (southwestern white pine), *P. caribaea* (Caribbean pine), *P. patula* (Mexican weeping pine), *P. tecumumanii* (Tecun Uman pine), *P. maximinoi*, *P. oocarpa* (Ocote Pine) and *P. chiapensis* (Mexican White pine). In addition, the current invention is specifically applicable to interspecies hybrids of the above mentioned pines including *Pinus rigida* x *P. taeda*, *P. serotina* x *P. taeda*, and reciprocal crosses.

It is preferred to utilize the present method with Southern yellow pines, *Pinus rigida*, and hybrids thereof. Those skilled in the art recognize that several species of pine indigenous to the Southeastern United States are closely related and hybridize naturally. Taxonomically this group of pines is referred to as "Southern yellow pines" and includes *Pinus taeda*, *P. serotina*, *P. palustris*, and *P. elliottii* (Preston 1989).

In addition to the taxonomically similarity of the above Southern yellow pine species, these species have also responded similarly in studies on somatic embryogenesis attempts. For example, all previous reports of somatic embryogenesis with the above species have found the same stage, very early precotyledonary zygotic embryos, to be optimum for embryogenic culture initiation (see, e.g., Becwar et al., 1990, and Jain et al. 1989).

An essential element of the present invention is the incorporation of activated carbon into media formulations used to develop stage 3 somatic embryos from conifer embryogenic cell cultures. A suitable level of activated carbon for use in improving the embryo development media for the methods taught in U.S. Pat. Nos. 5,413,930, 5,491,090, and 5,506,136 is from about 0.1 to about 10.0 grams per liter of medium (g/L) of medium. The preferred activated carbon level is about 0.5 to about 5.0 g/L.

A further essential element of the present invention is the incorporation of abscisic acid (ABA) into media formulations used to develop stage 3 somatic embryos from conifer embryogenic cell cultures. A suitable level of ABA for use in improving the embryo development media for the methods taught in U.S. Pat. Nos. 5,413,930, 5,491,090, and 5,506,136 is from about 110 to about 300 milligrams per liter of medium (mg/L) of medium. The preferred ABA level is from about 125 to about 250 mg/L.

Yet another essential element of the present invention is the maintenance of the high levels of ABA in the embryo development media. The preferred method of maintaining the ABA concentration is to transfer (subculture) the developing embryos onto fresh development medium containing an amount of abscisic acid equal to or greater than the amount present in the initial development medium. However, it is also possible to add additional ABA directly to the initial embryo development medium as needed in order to maintain the desired concentrations.

In addition to the activated carbon and the ABA, the embryo development medium also requires sufficient amounts of nutrients to allow the culture to remain viable. However, the present method is not limited to any single culture nutrient medium formulation. For example, four common basal culture media formulations which are suitable for use in the present method are listed in Table I below. However, it should be understood that any nutrient media commonly used in Pinus somatic embryogenesis will be suitable for use with this invention.

TABLE I

Formulations Of Basal Culture Media

| COMPONENT | $DCR^a$ | $SH^b$ | $WVS^c$ | $MSG^d$ |
|---|---|---|---|---|
| | \multicolumn{4}{c}{CONCENTRATION, mg/L} | | | |
| INORGANIC SALTS | | | | |
| $NH_4NO_3$ | 400.00 | — | 700.00 | — |
| $KNO_3$ | 340.00 | 2500.00 | 259.00 | 100.00 |
| $Ca(NO_3)_2.4H_2O$ | 556.00 | — | 963.00 | — |
| $MgSO_4.7H_2O$ | 370.00 | 400.00 | 1850.00 | 370.00 |
| $KH_2PO_4$ | 170.00 | — | 270.00 | 170.00 |
| $NH_4H_2PO_4$ | — | 300.00 | — | — |
| $CaCl_2.2H_2O$ | 85.00 | 200.00 | — | 440.00 |
| KCl | — | — | 1327.00 | 745.00 |
| KI | 0.83 | 1.00 | 0.83 | 0.83 |
| $H_3BO_3$ | 6.20 | 5.00 | 31.00 | 6.20 |
| $MnSO_4.H_2O$ | 22.30 | 10.00 | 15.16 | 16.90 |
| $ZnSO_4.7H_2O$ | 8.60 | 1.00 | 8.60 | 8.60 |
| $Na_2MoO_4.2H_2O$ | 0.25 | 0.10 | 0.25 | 0.25 |
| $CuSO_4.5H_2O$ | 0.25 | 0.20 | 0.25 | 0.03 |

TABLE I-continued

Formulations Of Basal Culture Media

| COMPONENT | DCR[a] | SH[b] | WV5[c] | MSG[d] |
|---|---|---|---|---|
| | \multicolumn{4}{c}{CONCENTRATION, mg/L} | | | |
| $CoCl_2.6H_2O$ | 0.03 | 0.10 | 0.03 | 0.03 |
| $NiCl_2.6H_2O$ | 0.03 | — | — | — |
| $FeSO_4.7H_2O$ | 27.80 | 15.00 | 27.80 | 27.80 |
| $Na_2EDTA$ | 37.30 | 20.00 | 37.30 | 37.30 |
| VITAMINS, AMINO ACIDS | | | | |
| Nicotinic acid | 0.50 | 0.5 | 0.50 | 0.50 |
| Pyridoxine.HCl | 0.50 | 0.5 | 0.50 | 0.10 |
| Thiamine.HCl | 1.00 | 1.00 | 1.00 | 0.10 |
| Glycine | 2.00 | 2.00 | 2.00 | — |

[a]) According to Gupta and Durzan (1985).
[b]) According to Schenk and Hildebrandt (1972).
[c]) According to Coke (1996).
[d]) According to Becwar et al. (1990).

Suitable media for use in improving the embryo development step for the methods taught in U.S. Pat. Nos. 5,413,930, 5,491,090, and 5,506,136 contain from about 20.0 to about 70.0 grams per liter (g/l) of a sugar selected from the group consisting of glucose, maltose, sucrose, melezitose, and combinations thereof.

Suitable media for use in improving the embryo development step for the methods taught in U.S. Pat. Nos. 5,413,930, 5,491,090, and 5,506,136 contain a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL® (an agar/gellan gum mixture commercially available from Sigma Chemical Company), and combinations thereof.

Suitable embryo development periods for use in the improved embryo development step for the methods taught in U.S. Pat. Nos. 5,413,930, 5,491,090, and 5,506,136 last for about 3 to 18 weeks; with the preferred period being about 8 to 12 weeks. The present method allows embryos to be developed from embryogenic tissue or suspension cultures which have been cryopreserved.

A number of terms are known to have differing meanings when used in the literature. The following definitions are believed to be the ones most generally used in the field of botany and are consistent with the usage of the terms in the present specification.

"Clone" when used in the context of plant propagation refers to a collection of individuals having the same genetic makeup.

"Corrosion cavity" is the cavity within the megagametophyte tissue of conifers formed by the growth and enlargement of the zygotic embryos.

"Conversion" refers to the acclimatization process that in vitro derived germinating somatic embryos undergo in order to survive under ex vitro (nonaxenic) conditions, and subsequent continued growth under ex vitro conditions.

"Cryopreservation" is storing cultures or tissues at ultralow temperatures (below about −120° C.) in a liquid nitrogen chamber for indefinite maintenance to prevent aging and loss of viability.

An "embryogenic culture" is a plant cell or tissue culture capable of forming somatic embryos and regenerating plants via somatic embryogenesis.

"Embryogenic tissue", in conifers, is a mass of tissue and cells comprised of very early stage somatic embryos and suspensor-like cells embedded in a mucilaginous matrix. The level of differentiation may vary significantly among embryogenic conifer cultures. In some cases, rather than containing well-formed somatic embryos, the embryogenic tissue may contain small, dense clusters of cells capable of forming somatic embryos. This has also been referred to as "embryogenic suspensor masses" by some researchers and is also called "embryogenic callus" in some of the conifer somatic embryogenesis literature; but most researchers believe it is not a true callus.

An "established" embryogenic liquid suspension culture is considered to be any culture that grows and can be maintained in a viable embryogenic state.

An "explant" is the organ, tissue, or cells derived from a plant and cultured in vitro for the purpose of starting a plant cell or tissue culture.

"Field planting" is the establishment of laboratory, greenhouse, nursery, or similarly grown planting stock under field conditions.

"Genotype" is the genetic constitution of an organism; the sum total of the genetic information contained in the chromosomes of an organism.

"Germination" is the emergence of the radicle or root from the embryo.

"Initiation" is the initial cellular proliferation or morphogenic development that eventually results in the establishment of a culture from an explant.

"Megagametophyte" is haploid nutritive tissue of the conifer seed, of maternal origin, within which the conifer zygotic embryos develop.

"Micropyle" is the small opening in the end of the conifer seed where the pollen tube enters the ovule during fertilization, and where embryogenic tissue extrudes from the megagametophyte during culture initiation.

"Nutrients" are the inorganics (e.g., nitrogen), vitamins, organic supplements, and carbon sources necessary for the nourishment of the culture.

A "plantlet" is a small germinating plant derived from a somatic embryo.

"Regeneration", in plant tissue culture, is a morphogenic response to a stimuli that results in the production of organs, embryos, or whole plants.

"Stage 1 embryos" are small embryos consisting of an embryonic region of small, densely cytoplasmic cells subtended by a suspensor comprised of long and highly vacuolated cells.

"Stage 2 embryos" are embryos with a prominent (bullet shaped) embryonic region that is more opaque and with a more smooth and glossy surface than stage 1 embryos.

"Stage 3 embryos" are embryos with an elongated embryonic region with small cotyledons visible.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic embryos; a region of small embryonal cells subtended by elongated suspensor cells. The embryonal cells develop into the mature somatic embryo.

A "suspension culture" is a culture composed of cells suspended in a liquid medium, usually agitated on a gyrotory shaker and is usually formed by placing embryogenic tissue in liquid medium. An embryogenic suspension culture in conifers is usually composed of early stage somatic embryos with well formed suspensor cells and dense cytoplasmic head cells that float freely in the liquid medium.

A "suspensor cell" is an extension of the base of the embryo that physically pushes the embryo into the megagametophyte in conifer seeds and is comprised of elongated and highly vacuolated cells. In a somatic embryo these elongated cells are cluster in rows and extend from the base of the dense cytoplasmic cells at the head or apex.

A "zygotic embryo" is an embryo derived from the sexual fusion of gametic cells.

The following examples are provided to further illustrate the present invention and are not to be construed as limiting the invention in any manner.

EXAMPLE 1

The methods claimed in U.S. Pat. Nos. 5,413,930 and 5,506,136 were followed in this example. However, a comparison study was run between the methods using the patented embryo development step and the methods employing the improved development step taught herein.

Immature seed cones were collected from several different loblolly pine (*Pinus taeda* L.) sources located in Westvaco's South Carolina coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium (see Table I, DCR).

Basal salt mixtures which have proven effective for culture initiation include the basal salts formulations listed in Table I. (The complete formulations of the media used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes.

The basal media modified for each of the culture stages are listed in Tables II and III below.

TABLE II

Composition Of Initiation and Maintenance Media Commonly Used In The Examples

| COMPONENT | Initiation Medium $DCR_1$ | Semi-Solid Maintenance Medium $DCR_1$ | Liquid Maintenance Medium $DCR_2$ |
|---|---|---|---|
| Basal medium[a] | DCR | DCR | DCR |
| | CONCENTRATION (g/l) | | |
| Inositol | 0.50 | 0.50 | 0.50 |
| Casein hydrolysate | 0.50 | 0.50 | 0.50 |
| Sucrose | 30.00 | 30.00 | 30.00 |
| GELRITE[b] | 1.25 | 2.00 | 0 |
| Activated Carbon | 0 | 0 | 0.5 |
| | CONCENTRATION (mg/l) | | |
| Auxin[c] | 3.00 | 3.00 | 3.00 |
| Cytokinin[d] | 0.50 | 0.50 | 0.50 |
| ABA[e] | 0.1–100.0 | 0.1–100.0 | — |

[a]) Refer to Table I for composition of basal medium.
[b]) GELRITE ® (gellan gum manufactured by Merck, Inc.)
[c]) 2,4-dichlorophenoxyacetic acid (2,4-D).
[d]) $N^6$-benzylaminopurine [or $N^6$-benzyladenine (BAP)].
[e]) (±) cis,trans-Abscisic acid.

TABLE III

Composition Of Development Media Used In The Examples

| COMPONENT | Predevelopment Medium | Development Medium $MSG_1$ |
|---|---|---|
| Basal medium[a] | $MSG_D$ | MSG |
| | CONCENTRATION (g/l) | |
| Inositol | 0.10 | 0.10 |
| L-glutamine | 1.45 | 1.45 |
| Sucrose | 30.00 | — |
| Maltose | — | 60.00 |
| GELRITE | 2.00 | 2.00 |
| Activated carbon | 5.0 | 0–1.25 |
| | CONCENTRATION (mg/l) | |
| ABA[b] | — | 22–150 |

[a]) Refer to Table I for composition of basal medium.
[b]) (±) cis,trans-Abscisic acid.

Embryogenic tissue cultures from two loblolly pine sources were initiated on semi-solid $DCR_1$ medium containing 3.0 mg/l 2,4-D, 0.5 mg/l BAP, and 0.125% GELRITE. Once cultures were extruded and subcultured, they were kept on the above medium but with the GELRITE concentration increased to 0.2%. After 6–18 months on this maintenance medium, the callus clumps were subcultured to $MSG_1$ development medium containing different levels of ABA ranging from 22 to 150 mg/l. There were seven different development treatments examined.

In treatment one, callus clumps were put in a development step using procedures taught in U.S. Pat. Nos. 5,413,930 and 5,506,136. Callus clumps were placed for one week on $MSG_p$ predevelopment medium containing no growth regulators but with 5 g/l activated carbon. After one week, the clumps were then switched to $MSG_1$ development medium containing 22 mg/l ABA.

In the other six treatments, callus clumps were placed directly on $MSG_1$ development medium containing 1.25 g/l activated carbon plus one of six different levels of ABA. These were 22, 50, 75, 100, 125 and 150 mg/l ABA. The control in this study was treatment one, which contained 22 mg/l of ABA with no activated carbon (as taught in U.S. Pat. Nos. 5,413,930 and 5,506,136). Callus clumps were transferred at 3 week intervals and at each transfer the callus clumps were placed on fresh medium containing the same level of ABA as was contained in the initial medium. The concentration of ABA was not decreased over time, as the clumps were placed back on media containing the same ABA level on which they were started. In other words the clumps were held at a constant level of ABA at each transfer. There were 6 clumps of callus placed on each treatment medium. After 6, 9 and 12 weeks on the development media, the stage 3 embryos were harvested from the callus clamps and counted. The results are listed in Table IV below.

TABLE IV

The Effect of Activated Carbon and High Levels of Abscisic Acid On the Development of Stage 3 Embryos

| Treatment # | 1 | 2 | 3 | 4 | 5 | 6 | 7 |
|---|---|---|---|---|---|---|---|
| | | | LEVEL OF ABA (MG/L) | | | | |
| LINE # | 22* | 22 | 50 | 75 | 100 | 125 | 150 |
| 1 | 0 | 2 | 10 | 7 | 4 | 7 | 3 |
| 2 | 82 | 56 | 105 | 157 | 256 | 240 | 283 |
| 3 | 128 | 77 | 86 | 87 | 122 | 168 | 127 |
| 4 | 104 | 125 | 105 | 73 | 126 | 195 | 239 |
| 5 | 96 | 89 | 40 | 29 | 56 | 71 | 86 |
| 6 | 312 | 210 | 271 | 247 | 495 | 574 | 484 |
| 7 | 191 | 129 | 173 | 183 | 232 | 198 | 176 |
| 8 | 41 | 46 | 63 | 33 | 45 | 91 | 72 |
| 9 | 78 | 36 | 41 | 60 | 49 | 61 | 84 |
| TOTAL | 1032 | 770 | 894 | 876 | 1385 | 1605 | 1554 |
| Average # embryos/ clump | 19.1 | 14.2 | 16.6 | 16.2 | 25.6 | 29.8 | 28.8 |

*Control containing no activated carbon.

Table IV displays the pooled totals of embryos harvested per line per development treatment. The results show that unusually high levels of ABA produced significantly higher numbers of stage 3 embryos. The best embryo production was produced using 125 and 150 mg/l ABA at constant levels throughout the development step. This is a significant improvement compared to the 11–22 mg/l levels taught in U.S. Pat. Nos. 5,413,930 and 5,506,136. These results were totally unexpected to those skilled in the art, in that it had been a common belief that such high levels of this growth regulator would be detrimental to embryogenic tissues (even with the presence of activated carbon in the medium).

EXAMPLE 2

The methods claimed in U.S. Pat. No. 5,491,090 were followed in this example. However, a comparison study was run between the methods using the patented embryo development step and the methods employing the improved development step taught herein.

Immature seed cones were collected from several different loblolly pine (*Pinus taeda* L.) sources located in Westvaco's South Carolina coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium (see Table I, DCR).

Basal salt mixtures which have proven effective for culture initiation include the basal salts formulations listed in Table I. (The complete formulations of the media used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes. The basal media modified for each of the culture stages are listed in Tables II and III above.

Embryogenic tissue cultures from two loblolly pine sources were initiated on semi-solid $DCR_1$ medium containing 3.0 mg/l 2,4-D, 0.5 mg/l BAP, and 0.125% GELRITE. Once cultures were extruded and subcultured, they were kept on the above medium but with the GELRITE concentration increased to 0.2%. After 10–18 months on this semi-solid maintenance medium, the callus clumps were placed in $DCR_2$ liquid maintenance medium containing 3 mg/l 2,4-D, 0.5 mg/l BAP, and 0.5 g/l activated carbon (as taught in U.S. Pat. No. 5,491,090). These were maintained by subculturing to fresh $DCR_2$ liquid medium every 1 to 2 weeks.

After 16 weeks in liquid culture, 3 lines from these two sources were plated on GELRITE-solidified $MSG_1$ development medium containing either 21 or 125 mg/l ABA to assess the ability of the cultures to develop high quality harvestable stage 3 embryos. A sterile 90 mm sterile NITEX nylon membrane disk (#3-35/16XX, commercially available from Tetko, Inc.) was placed in a sterile Buchner funnel. Three 40 mm nylon disks were placed on top of this larger nylon disk in the funnel equidistant from one another but not touching. One ml of suspension culture cells and medium were pipetted onto each of the 40 mm disks. The liquid medium was suctioned from the cells using a mild vacuum. Each 40 mm nylon disk with cells was removed from the Buchner funnel and placed on GELRITE solidified $MSG_1$ development medium (see Table II) in 100×25 mm plastic petri dishes. Dishes were incubated in a dark growth chamber at 23° C. The nylon disks were then transferred to new petri dishes containing fresh medium every 3 weeks. There were 3 disks of suspension culture cells from each line placed on each treatment medium.

At weeks 9–12, stage 3 embryos were counted and those deemed suitable for germination were harvested. There were two different development treatments examined. In treatment one, suspension culture cells were placed on $MSG_1$ development medium containing 21 mg/l ABA and no activated carbon. In treatment two, suspension culture cells were plated on $MSG_1$ development medium, with a high level of ABA plus activated carbon. The control in this study was treatment one, which contained 21 mg/l ABA but no activated carbon (as taught in U.S. Pat. No. 5,413,930).

The developing cell clumps were transferred at 3 week intervals and at each transfer the clumps were placed on fresh medium containing the same level of ABA. The concentration of ABA was not decreased over time, as the developing clumps were placed back on the ABA level on which they were started. In other words, the tissues were exposed to a constant level of ABA at each transfer. Embryos were developed from suspension culture cells cultured on $MSG_1$ development medium containing different ABA concentrations. A total of 3 one-ml aliquots were plated per line per ABA level. After 9–12 weeks on the respective development media, all of the stage 3 embryos were harvested and counted. (Stage 3 embryos were classified as those deemed capable of germination in subsequent steps.) The results are listed in Table V below.

TABLE V

The Effect of Activated Carbon and High Levels of Abscisic Acid on the Development of Stage 3 Embryos

| | LEVEL OF ABA (MG/L) | |
|---|---|---|
| LINE[a] | 21[b] | 125 + a.c.[c] |
| 10 | 49 | 187 |
| 11 | 54 | 159 |
| 12 | 233 | 496 |
| TOTAL | 336 | 842 |
| EMBRYOS PER DISK | 37.3 | 93.6 |

[a]These 3 lines each have excellent genetic potentials.
[b]This medium contained no activated carbon.
[c]These media contained 1.25 g/l activated carbon.

The results listed in Table V show that high levels of ABA coupled with activated carbon produced significantly larger numbers of stage 3 embryos. In the best embryo production method (using activated carbon and 125 mg/l ABA at constant levels throughout the development step) the average embryo production per clump increased by three times. This is a significant improvement compared to the results obtained using the 11–22 mg/l levels taught in U.S. Pat. No. 5,413,930.

EXAMPLE 3

Following the procedures taught in Example 2 above, immature seed cones were collected from one loblolly pine (*Pinus teada L.*) seed source located in Westvaco's South Carolina coastal breeding orchard near Charleston, S.C.

Immature seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium (see Table I, DCR).

Basal salt mixtures which have proven effective for culture initiation include the basal salts formulations listed in Table I. (The complete formulations of the media used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes. The basal media modified for each of the culture stages are listed in Tables II and III above.

Embryogenic tissue cultures from one loblolly pine source were initiated on semi-solid $DCR_1$ medium with 3.0 mg/l 2,4-D, 0.5 mg/l BAP, 0.125% GELRITE. Once cultures were extruded and subcultured, they were kept on the above medium but with the GELRITE concentration increased to 0.2%. The cultures were subsequently subcultured at three-week intervals by plating the embryogenic tissue on to fresh medium. After 8–20 months on this semi-solid maintenance medium, the callus clumps were placed on GELRITE-solidified $MSG_1$ development medium containing different levels of ABA ranging from 21 to 250 mg/l to assess the ability of the cultures to develop high quality harvestable stage 3 embryos. There were six different development treatments examined. There were 3 clumps of callus placed on each treatment medium.

At weeks 8–9, stage 3 embryos were counted and those deemed suitable for germination were harvested. There were six different development treatments examined. In treatment one, suspension culture cells were placed on MSG$_1$ development medium containing 21 mg/l ABA and no activated carbon. In the other five treatments, callus cells were plated on MSG$_1$ development medium containing 1.25 g/l activated carbon plus 5 different levels of ABA. These were 21, 50, 100, 150, 200, and 250 mg/l ABA. The control in this study was treatment one, with 21 mg/l ABA with no activated carbon as taught in U.S. Pat. No. 5,413,930.

The developing cell clumps were transferred at 3 week intervals and at each transfer the clumps were placed on fresh medium containing the same level of ABA. The concentration of ABA was not decreased over time since developing clumps were placed back on the level on which they were started. In other words the tissues were exposed to a constant level of ABA at each transfer. Embryos were developed from callus culture cells cultured on MSG$_1$ development medium containing different ABA concentrations. After 8–9 weeks on the respective development media, all stage 3 embryos were harvested and counted. The average embryo production per clumps is listed in Table VI below.

TABLE VI

The Effect of Activated Carbon and High Levels of Abscisic Acid on the Development of Stage 3 Embryos

| LINE | LEVEL OF ABA (MG/L) | | | | | |
|---|---|---|---|---|---|---|
| | 22* | 50 | 100 | 150 | 200 | 250 |
| 15 | 11.7 | 13.3 | 11.7 | 42.7 | 38.3 | 34.3 |

*Control containing no activated carbon.

The results listed in Table VI again show that the use of extremely high levels of ABA coupled with activated carbon produced more stage 3 embryos. For this line, embryo production increased from around 12 embryos per clump to about 43 embryos per clump at the most effective ABA (i.e., using 150 mg/l ABA at constant levels during the development process).

Many modifications and variations of the present invention will be apparent to one of ordinary skill in the art in light of the above teachings. It is therefore understood that the scope of the invention is not to be limited by the foregoing description, but rather is to be defined by the claims appended hereto.

BIBLIOGRAPHY

Becwar, M. R., E. E. Chesick, L. W. Handley, M. R. Rutter. Method for regeneration of coniferous plants by somatic embryogenesis U.S. Pat. No. 5,413,930—issued May 9, 1995.

Becwar, M. R., E. E. Chesick, L. W. Handley, M. R. Rutter. Method for regeneration of coniferous plants by somatic embryogenesis. U.S. Pat. No. 5,506,136—issued Apr. 9, 1996.

Becwar, M. R., R. Nagmani, and S. R. Wann. Initiation of embryogenic cultures and somatic embryo development in loblolly pine (*Pinus taeda*). *Canadian Journal of Forest Research* 20:810–817, 1990.

Coke, J. E. Basal Nutrient Medium for In Vitro Cultures of Loblolly Pines. U.S. Pat. No. 5,534,433—issued Jul. 9, 1996.

Gupta, P. K. and D. J. Durzan. Shoot multiplication from mature trees of Douglas-fir (*Pseudotsuga menziesii*) and sugar pine (*Pinus lambertiana*). *Plant Cell Reports* 4:177–179, 1985.

Gupta, P. K. and G. S. Pullman. Method for reproducing coniferous plants by somatic embryogenesis. U.S. Pat. No. 4,957,866—issued Sep. 18, 1990.

Gupta, P. K. and G. S. Pullman. Method for reproducing coniferous plants by somatic embryogenesis using abscisic acid and osmotic potential variation. U.S. Pat. No. 5,036,007—issued Jul. 30, 1991.

Gupta, P. K. and G. S. Pullman. Method for reproducing coniferous plants by somatic embryogenesis using stepwise hormone adjustment U.S. Pat. No. 5,236,841—issued Aug. 7, 1993.

Hakman, I. and S. von Arnold. Plantlet regeneration through somatic embryogenesis in *Picea abies* (Norway spruce). *Journal of Plant Physiology* 121:149–158, 1985.

Hakman, I., L. C. Fowke, S. von Arnold, and T. Eriksson. The development of somatic embryos in tissue cultures initiated from immature embryos of *Picea abies* (Norway spruce). *Plant Science* 38:53–59, 1985.

Handley, L. W., M. R. Becwar, E. E. Chesick, J. E. Coke, A. P Godbey and M. R. Rutter. Research and Development of commercial tissue culture systems in loblolly pine, *Pinus taeda* L. Proceedings TAPPI 1994 Biological Sciences Symposium. Oct. 3–6, 1994. pp. 169–175. TAPPI Press 1994.

Handley, L. W. and A. P Godbey. Embryogenic Coniferous Liquid Suspension Cultures. U.S. Pat. No. 5,491,090—issued Feb. 13, 1996.

Jain, S. M., N. Dong, and R. J. Newton. Somatic embryogenesis in slash pine (*Pinus elliottii*) from immature embryos cultured in vitro. *Plant Science* 65:233–241, 1989.

Preston, R. J. North American Trees, 4th edition. Iowa State Univ. Press, Ames. pp. 4–7, 1989.

Pullman, G. S. and P. K. Gupta. Method for reproducing coniferous plants by somatic embryogenesis using adsorbent materials in the development stage media. U.S. Pat. No. 5,034,326—issued Jul. 23, 1991.

Pullman, G. S. and P. K. Gupta. Method for reproducing conifers by somatic embryogenesis using mixed growth hormones for embryo culture. U.S. Pat. No. 5,294,549—issued Mar. 15, 1994.

Roberts, D. R. Process for the production, desiccation and germination of conifer somatic embryos. U.S. Pat. No. 5,183,757—issued Feb. 2, 1993.

Schenk, R. U. and A. C. Hildebrandt. Medium and techniques for induction and growth of monocotyledonous and dicotyledonous plant cell cultures. *Canadian Journal of Botany* 50:199–204, 1972.

Tautorus, T. E., L. C. Fowke, and D. I. Dunstan. Somatic embryogenesis in conifers. *Canadian Journal of Botany* 69:1873–1899, 1991.

Uddin, M. Somatic embryogenesis in gymnosperms. U.S. Pat. No. 5,187,092—issued Feb. 16, 1993.

von Arnold, S. and I. Hakman. Regulation of somatic embryo development in *Picea abies* by abscisic acid (ABA). *Journal of Plant Physiology* 132:164–169, 1988.

What is claimed is:

1. An improved method for reproducing plants selected from the group consisting of *Pinus taeda, Pinus serotina, Pinus palustris, Pinus elliottii, Pinus rigida,* and hybrids thereof, by somatic embryogenesis which comprises:

(a) placing a suitable explant selected from the group consisting of immature zygotic embryos and megagametophytes containing immature zygotic embryos on culture initiation medium containing a sufficient amount of nutrients, 0.1 to 5.0 mg/L of auxin, 0.1 to 1.0 mg/L of cytokinin, 10.0 to 40.0 g/L of a sugar selected from the group consisting of glucose, maltose, sucrose, melezitose, and combinations thereof, a gelling agent selected from the group consisting of 2.5 to 4.5 g/L of agar, 0.5 to 1.5 g/L of gellan gum, 3.0 to 5.0 g/L of agarose, and combinations thereof, for 2 to 14 weeks under suitable environmental conditions to grow a culture containing embryogenic tissue;

(b) transferring the embryogenic tissue culture to culture maintenance medium containing a sufficient amount of nutrients, 0.1 to 5.0 mg/L of auxin, 0.1 to 1.0 mg/L of cytokinin, 10.0 to 40.0 g/L of a sugar selected from the group consisting of glucose, maltose, sucrose, melezitose, and combinations thereof, and a gelling agent selected from the group consisting of 6.0 to 9.0 g/L of agar, 1.75 to 3.50 g/L of gellan gum, 6.0 to 8.0 g/L of agarose, and combinations thereof, for a sufficient time under suitable environmental conditions to develop a mass of embryogenic tissue having a weight of at least about 100.0 mg;

(c) transferring at least about 100.0 mg of the mass of embryogenic tissue to embryo development medium containing a sufficient amount of nutrients, a gelling agent selected from the group consisting of 6.0 to 12.0 g/L of agar, 1.75 to 4.00 g/L of gellan gum, 6.0 to 8.0 g/L of agarose, and combinations thereof, and 20.0 to 70.0 g/L of a sugar selected from the group consisting of glucose, maltose, sucrose, and combinations thereof, and wherein the improvement comprises the addition of about 0.1 to about 10.0 g/L of activated carbon, the addition of about 125.0 to about 300.0 mg/L of abscisic acid, and the continued maintenance of the abscisic acid concentration at said level, for a sufficient time under suitable environmental conditions to develop stage 3 somatic embryos;

(d) separating the stage 3 somatic embryos from the development medium and partially drying the embryos by exposing the embryos to an atmosphere having a high relative humidity for sufficient time to permit the embryos to lose about 25% to 75% of their pre-dried weight;

(e) transferring the partially dried somatic embryos to germination medium containing a sufficient amount of nutrients, up to 10.0 g/L of activated carbon, a gelling agent selected from the group consisting of 6.0 to 9.0 g/L of agar, 1.75 to 3.50 g/L of gellan gum, 6.0 to 8.0 g/L of agarose, and combinations thereof, and 20.0 to 40.0 g/L of a sugar selected from the group consisting of glucose, maltose, sucrose, and combinations thereof, for a sufficient time under suitable environmental conditions to germinate the partially dried embryos;

(f) converting the germinated embryos into acclimatized plants; and (g) field planting the acclimatized plants.

2. The method of claim 1 wherein the embryo development medium contains from about 0.5 to about 5.0 g/L of activated carbon.

3. The method of claim 1 wherein the embryo development medium contains from about 125 to about 250 mg/L of abscisic acid.

4. The method of claim 1 wherein the abscisic acid concentration in the embryo development medium is continually maintained over time by again transferring the embryogenic tissue at least once to a fresh embryo development medium containing an amount of abscisic acid which is at least equal to the amount of abscisic acid initially present in the first embryo development medium.

5. The method of claim 1 wherein the abscisic acid concentration in the embryo development medium is continually maintained over time by adding additional abscisic acid to the embryo development medium.

6. The method of claim 1 wherein the embryogenic tissue has been cryopreserved.

7. An improved method for reproducing plants selected from the group consisting of Pinus taeda, Pinus serotina, Pinus palustris, Pinus elliottii, Pinus rigida, and hybrids thereof, by somatic embryogenesis which comprises:

(a) placing a suitable explant selected from the group consisting of immature zygotic embryos and megagametophytes containing immature zygotic embryos on culture initiation medium containing a sufficient amount of nutrients, 0.1 to 5.0 mg/L of auxin, 0.1 to 1.0 mg/L of cytokinin, 5.0 to 100.0 g/L of a sugar selected from the group consisting of glucose, maltose, sucrose, melezitose, and combinations thereof, a gelling agent selected from the group consisting of 2.5 to 4.5 g/L of agar, 0.5 to 1.5 g/L of gellan gum, 3.0 to 5.0 g/L of agarose, and combinations thereof, for 2 to 14 weeks under suitable environmental conditions to grow a culture containing embryogenic tissue;

(b) transferring the embryogenic tissue culture to liquid suspension culture maintenance medium containing a sufficient amount of nutrients, 0.1 to 100.0 mg/L of auxin, 0.05 to 10.0 mg/L of cytokinin, 5.0 to 100.0 g/L of a sugar selected from the group consisting of glucose, maltose, sucrose, melezitose, and combinations thereof, and about 0.1 to about 10.0 g/L of activated carbon, for a sufficient time under suitable environmental conditions to develop a liquid embryogenic cell culture;

(c) transferring at least 30.0 mg of the liquid embryogenic cell culture to embryo development medium containing a sufficient amount of nutrients, a gelling agent selected from the group consisting of 6.0 to 12.0 g/L of agar, 1.75 to 4.00 g/L of gellan gum, 6.0 to 8.0 g/L of agarose, and combinations thereof, and 20.0 to 70.0 g/L of a sugar selected from the group consisting of glucose, maltose, sucrose, and combinations thereof, and wherein the improvement comprises the addition of about 0.1 to about 10.0 g/L of activated carbon, the addition of about 125.0 to about 300.0 mg/L of abscisic acid, and the continued maintenance of the abscisic acid concentration at said level, for a sufficient time under suitable environmental conditions to develop stage 3 somatic embryos;

(d) separating the stage 3 somatic embryos from the development medium and partially drying the embryos by exposing the embryos to an atmosphere having a high relative humidity for sufficient time to permit the embryos to lose about 25% to 75% of their pre-dried weight;

(e) transferring the partially dried somatic embryos to germination medium containing a sufficient amount of nutrients, up to 10.0 g/L of activated carbon, a gelling agent selected from the group consisting of 6.0 to 9.0 g/L of agar, 1.75 to 3.50 g/L of gellan gum, 6.0 to 8.0 g/L of agarose, and combinations thereof, and 20.0 to 40.0 g/L of a sugar selected from the group consisting of glucose, maltose, sucrose, and combinations thereof for a sufficient time under suitable environmental conditions to germinate the partially dried embryos;

(f) converting the germinated embryos into acclimatized plants; and (g) field planting the acclimatized plants.

8. The method of claim 7 wherein the embryo development medium contains from about 0.5 to about 5.0 g/L of activated carbon.

9. The method of claim 7 wherein the embryo development medium contains from about 125 to about 250 mg/L of abscisic acid.

10. The method of claim 7 wherein the abscisic acid concentration in the embryo development medium is continually maintained over time by again transferring the embryogenic tissue at least once to a fresh embryo development medium containing an amount of abscisic acid which is at least equal to the amount of abscisic acid initially present in the first embryo development medium.

11. The method of claim 7 wherein the abscisic acid concentration in the embryo development medium is continually maintained over time by adding additional abscisic acid to the embryo development medium.

12. The method of claim 7 wherein the embryogenic tissue has been cryopreserved.

* * * * *